ent Number: 4,594,880
Date of Patent: Jun. 17, 1986

United States Patent
Murdoch et al.

[54] APPARATUS FOR DETERMINING FINISHED ROLL DENSITY IN A MILL

[75] Inventors: James C. Murdoch, Cavan; Clarence J. Klassen, Peterborough, both of Canada

[73] Assignee: Canadian General Electric Company Limited, Toronto, Canada

[21] Appl. No.: 686,695

[22] Filed: Dec. 27, 1984

[30] Foreign Application Priority Data

Dec. 14, 1984 [CA] Canada .................................. 470173

[51] Int. Cl.⁴ ............................................. G01N 9/00
[52] U.S. Cl. .................................... 73/32 R; 364/558
[58] Field of Search ............... 73/32 R, 159; 162/263; 364/471, 571, 560, 561, 558

[56] References Cited

FOREIGN PATENT DOCUMENTS 705626  3/1965  Canada .

OTHER PUBLICATIONS

"Measurement of Paper Roll Density During Winding", L. G. Eriksson et al., Tappi Journal, Jan. 1983, pp. 63–66.

*Primary Examiner*—Stewart J. Levy
*Assistant Examiner*—Robert R. Raevis
*Attorney, Agent, or Firm*—Raymond A. Eckersley

[57] ABSTRACT

In the prior art it is known to determine the density of a roll of paper as it is being wound on a paper receiving roll. The determination is made each time the paper receiving roll makes a constant predetermined number of revolutions. Because the diameter of the paper on the paper receiving roll increases, there is an increasing length of paper added between successive determinations. This makes it more difficult to maintain a desired roll density by controlling various factors during winding. In addition, because the paper web is usually fed onto the roll at a constant rate, the time between successive density determinations increases. The system of the invention provides for an adjustment of the predetermined number of revolutions between density determinations. This number is decremented to provide, very approximately, the same time interval between successive determinations. This change in the number of revolutions of the paper receiving roll between predetermined calculations of roll density complicates the determinations made because the length of paper and change in diameter are both different between successive determinations. The apparatus detects these changes and incorporates the changes to get average values for use in calculations to provide a determination of roll density at intervals based on a substantially constant length of paper wound onto the paper receiving roll.

5 Claims, 3 Drawing Figures

APPARATUS FOR DETERMINING FINISHED ROLL DENSITY IN A MILL

BACKGROUND OF THE INVENTION

This invention relates to apparatus for determining roll density in a paper mill, or more particularly for determining roll density in a paper winder or paper winding means used in a paper mill or the like.

Paper roll density (which for most purposes may be assumed to be proportional to roll hardness, at least over the range of interest) is a parameter of considerable interest in the winding of a roll. The density of the outermost layers are of particular interest in that they influence the structure of the completed roll. The density of the outer layers as they are added to the roll during winding is not the same as the density of the finished roll because as the winding progresses the previous outer layers are covered and there is radial pressure now added by the new outer layers.

A number of factors affect roll density and these factors include radial internal pressure (which is difficult to measure directly), web tension, rider roll pressure and drum torque. By monitoring roll density continuously during winding, it is possible to detect errors in the build-up of the roll and to correct the errors or at least be aware of the errors to ensure that unsatisfactory rolls are not shipped.

Various means have been developed to monitor roll density. One such means determines the volume of paper added to the roll by counting the number of revolutions of the paper roll since the last determination and using this with a measurement of paper length to obtain roll diameter. Then roll diameter, or certain of the measurements used to obtain roll diameter, and paper length are used to obtain density. An article entitled "Measurement of Paper Roll Density During Winding" by L. G. Eriksson et al, TAPPI Journal, January, 1983, pages 63–66, describes one form of such a manner of determining roll density.

The determination of roll density is better understood by reference to FIG. 1 which shows one form of prior art apparatus for determing roll density. In FIG. 1, a first and a second drum 10 and 11 support a finished paper roll 12. A web of paper 13 passes under drum 10 and is wound on roll 12. Pulse transmitters 14 and 15 are on drum 10 and roll 12 respectively, and they transmit pulses on conductors 16 and 17 respectively which are proportional to rotation. For example, the number of pulses from transmitter 14 might be of the order of 5000 ppr (pulses per revolution) and will be designated Z hereinafter, and the number of pulses from transmitter 15 might be of the order of one ppr and will be designated V hereinafter. The diameter of roll 12 increases as paper is wound on it. Because the rate of feeding the paper onto roll 12 is substantially constant, that is the speed of drum 10 is approximately constant, the rate of rotation of roll 12 decreases as its diameter increases.

Conductor 17 is connected to a first counter 18 which has set into it at 20 a count N which is the number of pulses received on conductor 17 before counter 18 outputs a pulse on conductor 21. For example N might be set to a value of 50 and if V=1 then there would be 50 revolutions of roll 12 for each pulse on conductor 21. Similarly conductor 16 is connected to a second counter 22 which counts pulses from transmitter 14 and provides an output on conductor 23. The count on conductor 23 represents paper length L.

A number of values are set into the apparatus at input 24. These values include the previously referred to Z and N, and also m=paper basis weight, that is the weight of paper per unit area
$D_D$=diameter of the first drum 10.

The count of pulses on conductor 21 may be represented by K and the count is set to one, i.e. K=1 is preset in block 24 before starting. The paper length L is also initialized in block 24 before starting by setting L(K)=0, that is by setting the paper length to zero for the Initial reading or initial count K=1.

A start circuitry 26 provides a signal on conductor 27 when it receives a pulse on conductor 21. This starts the monitoring apparatus. The start circuitry 26 also includes a counter which keeps track of the number of pulses received from conductor 21. Each pulse increments K by one.

Conductor 27 is connected to read pulse counter block 28. Each time the read pulse counter block 28 receives a signal from conductor 27 it reads the count from counter 22 and stores the value. Thus it has the values for the length at each reading K, i.e. it has L(K), L(K+1) and so on. The read pulse counter 28 provides a signal on conductor 30 representing the count which in turn represents paper length at the current reading K. A decision circuit 31 receives the signal on conductor 30 and determines if K is equal to or greater than three. If not, it provides a signal on conductor 32 back to the start block 26. The purpose of this is to provide values for averaging. At least two pulses on conductor 21 are required to initiate a calculation. In this case two sets of readings are available for averaging.

When decision circuit 31 receives a signal on conductor 30 and the value of K is equal to or greater than three, it provides a signal to the calculate roll diameter circuitry 33. While roll diameter is not as difficult to determine as roll density (and in the prior art it has been determined by measurement as well as by calculation), it is a convenient value to know. For example, a plot of roll density vs. roll diameter provides a useful display to an operator during winding or provides a useful graph for analysis. In addition many of the values required to calculate roll diameter are required to calculate roll density. It will also be apparent that two successive roll diameter determinations can be subtracted to give a diameter difference, and if the number of turns are known a thickness of the paper can be calculated. Knowing paper length and paper basis weight, enables a determination of roll density to be made. The calculate roll density circuitry 34 receives a signal from calculate roll diameter circuitry 33 and initiates a density determination. Signals representing both the determined value for roll diameter and for roll density are provided on conductor 35 which is connected to output results circuit 36.

In this prior art apparatus, the initiation of each reading and the calculations which are initiated depend on the pulses on conductor 21. These pulses depend on a fixed number of revolutions made by the paper roll 12. Thus, the pulses are relatively rapid when the winding starts because the diameter is small and the roll rotates relatively rapidly. As the diameter of the roll increases, its rate of rotation decreases and the time between readings increases. However, there is more paper wound on the roll for each revolution of the roll because of the increasing diameter. Consequently, the actual time between each determination of density increases as the roll of paper is wound, and a greater amount of paper is added to the roll. Thus, as the roll gets longer, the opportunities to make corrections between calculations become farther apart. This is undesirable.

SUMMARY OF THE INVENTION

According to the invention, the value used for N is decremented at intervals. Preferably, it is decremented based on a preselected length of paper being wound onto the finished paper receiving roll. In other words, the value for N that was originally set into counter 18 is decremented at intervals. Because the rate of paper feed onto the finished paper roll 12 is normally a substantially constant feed rate, the decreased values for N tend to provide density determinations at more or less constant time intervals.

It is therefore an object of the invention to provide an improved apparatus for determining roll density of a roll on a paper winding means.

It is another object of the invention to provide an apparatus which determines density at intervals which are substantially regular intervals as a roll of paper is wound.

DESCRIPTION OF THE PREFERRED EMBODIMENT

Figure 1:
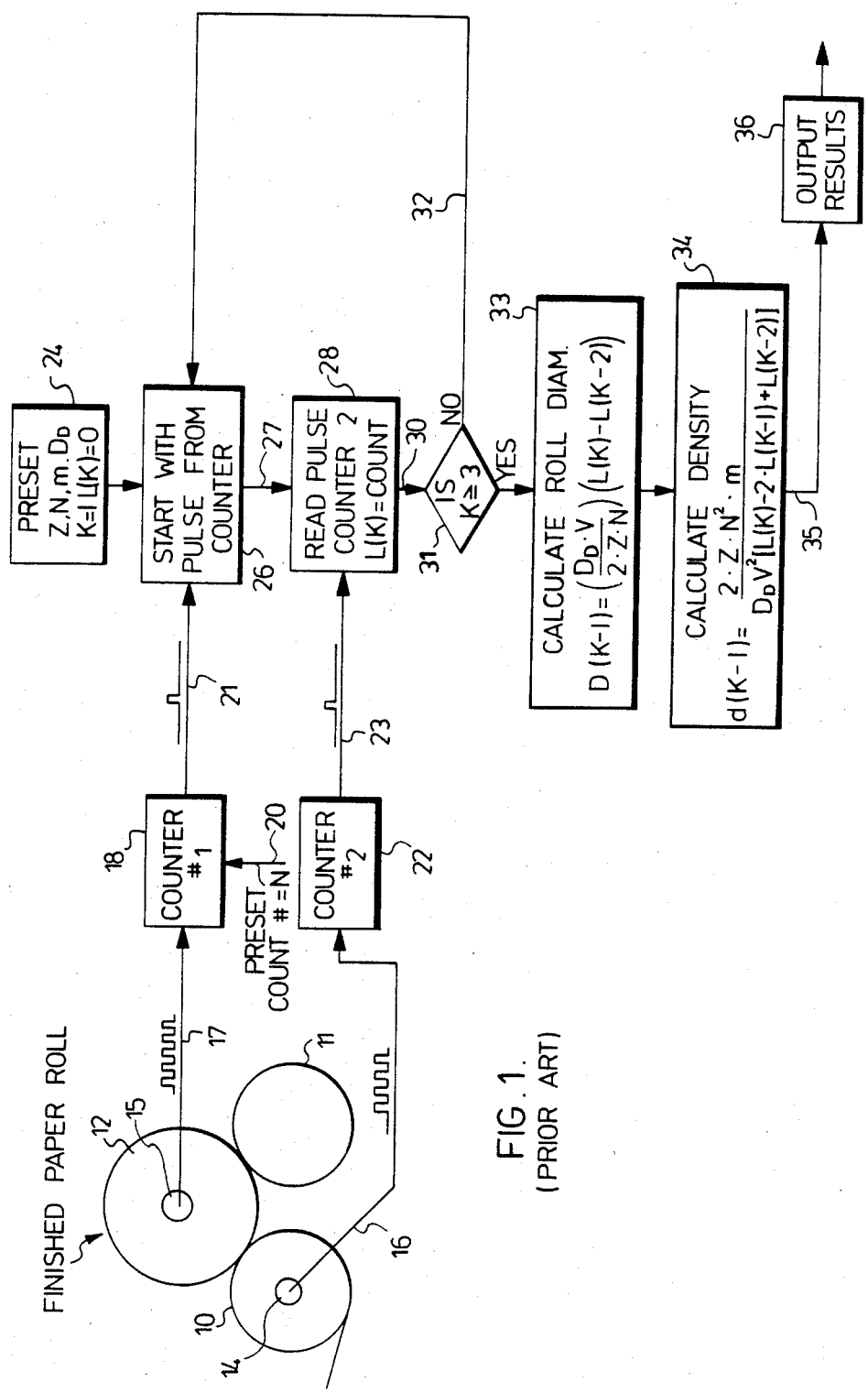
FIG. 1 is a simplified block schematic drawing showing a prior art apparatus for determining density in a paper roll.
Figures 2, 3:
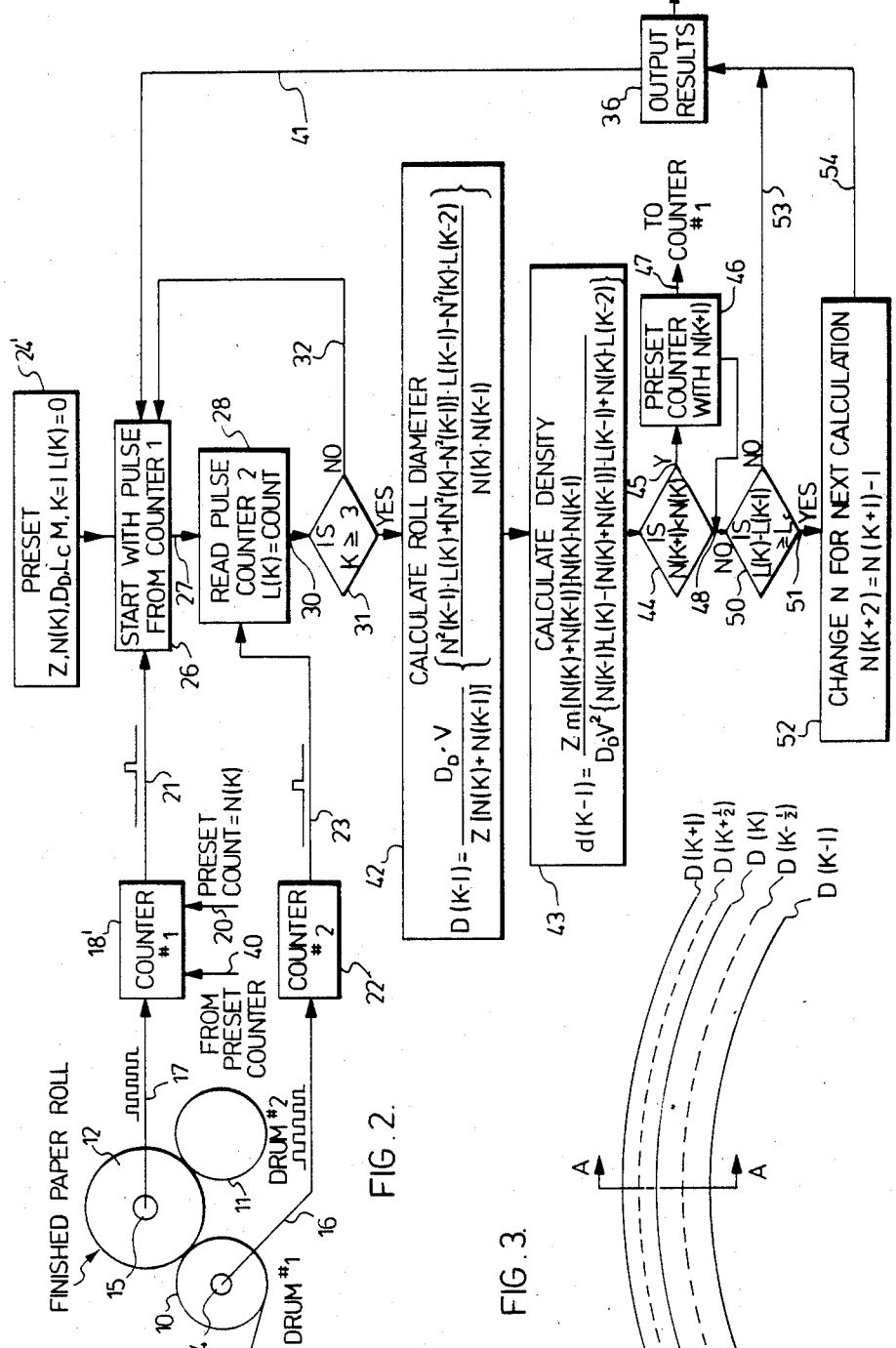
FIG. 2 is a simplified block schematic drawing showing apparatus according to the invention for determining density in a paper roll.
FIG. 3 is a sketch useful in explaining the invention.

In FIG. 2 many of the parts are the same as in FIG. 1 and serve the same purpose. These have been given the same designation numbers. Other parts with a very minor difference have been given the same numbers with a primed symbol.

The first drum 10 and the paper roll 12 with their respective rotation transmitters 14 and 15 in FIG. 2 are the same as in the prior art FIG. 1, and the same signals are on conductors 16 and 17. The second counter 22 is the same and conductor 23 carries the same pulse signal. The first counter 18° has two inputs. The first input 20 sets into the first counter 18' a value N(K) which is the starting value of N. In FIG. 2 this value N is decremented at intervals during the determination of density. This is to compensate for, or at least partly compensate for, the increased time between the pulses on conductor 17 as the paper roll 12 increases in size. Thus the input 40 on counter 18' changes the count made by counter 18' before it outputs a pulse on conductor 21.

As before, a number of values are set into the apparatus at input 24'. As the number N is changed according to the invention, the starting value N(K) is set in at input 24'. This is updated periodically at input 40 as will be mentioned hereinafter. In addition, a new constant $L_c$ is set in to preset block 24'. This value is used to determine the point at which N(K) can be decremented and still maintain reasonable accuracy. It is a value determined in practice. Too small a value for this paper length constant $L_c$ will result in too many calculations for which the time may be insufficient, and too large a value lowers accuracy.

Also as before, the start block 26 outputs a pulse on conductor 27 when it receives a pulse on conductor 21. This initiates the circuitry of read pulse counter block 28 which sets L(K) equal to the count of the pulses on conductor 23. The decision circuit block 31 provides an output on conductor 32 if K is less than 3. Conductor 32 is connected to start circuitry 26 (which includes a counter for counting the K's) to provide the "No" signal as a check. If K is greater than or equal to 3 then the calculation of roll diameter is initiated by calculate roll diameter circuitry 42.

The roll diameter calculation may be explained with reference to FIG. 3 where a side view of a small portion of a roll of paper is shown.

Considering the interval from K−1 to K, the length of paper added to roll 12 (FIGS. 1 and 2) in that interval is $$\frac{\pi \cdot D_D}{Z} [L(K) - L(K - 1)]$$

Because the paper roll 12 (FIGS. 1 and 2) travels the same distance $$\frac{\pi \cdot D_D}{Z} [L(K) - L(K-1)] = \frac{\pi}{V} \cdot \left[ \frac{D(K) + D(K - 1)}{2} \right] \cdot N(K) \quad (1)$$

If we let $D\left(K - \frac{1}{2}\right) = \frac{D(K) + D(K - 1)}{2}$ (2)

then $$D\left(K - \frac{1}{2}\right) = \frac{D_D \cdot V}{Z \cdot N(K)} [L(K) - L(K -1)] \quad (3)$$

For the interval K to K+1 equation (3) becomes $$D\left(K + \frac{1}{2}\right) = \frac{D_D \cdot V}{Z \cdot N(K + 1)} [L(K + 1) - L(K)] \quad (4)$$

Thus for diameter D(K) along the roll diameter A—A in FIG. 3, it follows that $$D(K) = \frac{N(K) \cdot D(K + \frac{1}{2}) + N(K + 1) \cdot D(K - \frac{1}{2})}{N(K) + N(K + 1)} \quad (5)$$

Substituting (3) and (4) into (5)

$$D(K) = \frac{D_D \cdot V}{Z} \left\{ \frac{\frac{N(K) \cdot [L(K + 1) - L(K)]}{N(K + 1)} + \frac{N(K + 1) \cdot [L(K) - L(K - 1)]}{N(K)}}{N(K) + N(K + 1)} \right\} \quad (6)$$

$$= \frac{D_D \cdot V}{Z} \left\{ \frac{N^2(K) \cdot [L(K + 1) - L(K)] + N^2(K + 1) \cdot [L(K) - L(K - 1)]}{[N(K) + N(K + 1)] \cdot N(K + 1) \cdot N(K)} \right\} \quad (7)$$

$$= \frac{D_D \cdot V}{Z} \left\{ \frac{N^2(K) \cdot L(K+1) + [N^2(K+1) - N^2(K)] \cdot L(K) - N^2(K+1) \cdot L(K-1)}{[N(K) + N(K+1)] \cdot N(K+1) \cdot N(K)} \right\} \quad (8)$$

Therefore, after the reading L(K) is made, D(K−1) can be calculated $$D(K-1) = \frac{D_D \cdot V \cdot N^2(K-1) \cdot L(K) + N^2(K) - N^2(K-1) \cdot L(K-1) - N^2(K) + L(K-2)}{Z[N(K) + N(K-1)] \cdot N(K) \cdot N(K-1)} \quad (9)$$

It will be seen that all the values are available to calculate roll diameter. The calculation is for K−1 following reading K. This is necessary, of course, because of the averaging.

The roll density calculation is made by the calculate roll density circuitry 43 and may be explained generally as follows:

Considering first the average thickness t(K) of a single layer of paper throughout the region between D(K−½) and D(K+½) as represented in FIG. 3, $$t(K) = \frac{\left[ D\left(K + \frac{1}{2}\right) - D\left(K - \frac{1}{2}\right) \right]}{2} \cdot \frac{2 \cdot V}{[N(K) + N(K+1)]} \quad (10)$$

that is, the difference in diameters divided by two thickness per wrap times the reading V divided by the average N.

Now the density is equal to the paper basis weight m over thickness or $$d(K) = \frac{m}{t(K)} \quad (11)$$

$$d(K) = \frac{m \cdot [N(K) + N(K+1)]}{V \cdot [D(K+\frac{1}{2}) - D(K-\frac{1}{2})]} \quad (12)$$

Substituting equations (3) and (4) into (12)

$$d(K) = \frac{m \cdot N(K) + N(K+1)}{\frac{V \cdot D_D \cdot V \cdot L(K+1) - L(K)}{Z \cdot N(K+1)} - \frac{D_D \cdot V \cdot L(K) - L(K-1)}{Z \cdot N(K)}} \quad (13)$$

$$= \frac{m \cdot Z \cdot [N(K) + N(K+1)] \cdot N(K) + N(K+1)}{D_D \cdot V^2 \{N(K) \cdot [L(K+1) - L(K)] - N(K+1)[L(K) - L(K-1)]\}} \quad (14)$$

$$= \frac{m \cdot Z \cdot [N(K) + N(K+1)] \cdot N(K) + N(K+1)}{D_D \cdot V^2 \{N(K) \cdot L(K+1) - [N(K) + N(K+1)] \cdot L(K) + N(K+1) \cdot L(K-1)]\}} \quad (15)$$

After the reading L(K) is made, then d(K−1) can be determined.

$$d(K-1) = \frac{Z \cdot m \cdot [N(K) + N(K-1)] \cdot N(K) \cdot N(K-1)}{D_D \cdot V^2 \cdot \{N(K-1) \cdot L(K) - [N(K) + N(K-1)] \cdot L(K-1) + N(K) \cdot L(K-2)\}} \quad (16)$$

The value for roll density can thus be determined periodically, but means are necessary for decrementing N at intervals according to the invention.

Decision circuitry 44 provides an output on conductor 45 if N(K+1) is less than N(K), that is it determines if the value for the next N has decreased and an output signal is applied on conductor 45 to a preset counter block 46. The actual value for N does not necessarily change each time K is incremented and a new set of readings is taken. In other words as N changes with the succeeding counts of K, from N(K) to N(K+1) to N(K+2) and so on, the actual value which N represents does not necessarily decrease with each increment for K. Thus decision circuit 44 determines if there has been a decrease and if so it provides a signal on conductor 47 which is connected to input 40 on counter 18' and the count number in counter 18' is decremented. If N(K+1) is not less than N(K) the decision circuit 44 provides a signal on conductor 48 to decision circuit 50. Conductor 48 is also connected to circuitry in preset counter block 46. Block 46 also provides a signal on conductor 48 when the signal is provided on conductor 47 to change the count number in counter 18'.

The decision circuit 50 provides two outputs, one on conductor 51 and one on conductor 53. If L(K)−L(K−1) is less than the predetermined constant length $L_c$ there is an output on conductor 53 which is connected to the output results circuit 36. The output results circuit 36 may provide a control signal representing roll density and roll diameter, and more commonly it may provide a display of these values for an operator. It may also provide a signal for a record and the output for the record would include, for example, values for roll diameter, roll density and N, and might in addition include, for example, a time reference, and a paper speed value. In any case, the output includes a signal representing roll density.

L(K)−L(K−1) is equal to or greater than $L_c$ then the decision circuit 50 outputs a signal on conductor 51 to the circuitry of change N block 52. The change N block 52 sets the new N value, i.e. N(K+2), as indicated in FIG. 2 by N(K+2)=N(K+1)−1. This is in accordance with the previously mentioned set of N values. The circuitry of change N block 52 then outputs this value on conductor 54 to the output results circuit 36. The ouptut results circuit 36 then outputs the new value.

Conductor 41 connects the output results circuit 36 with the start circuitry 26 and provides the new value for N, i.e. N(K+2). It should be noted that N is decremented, e.g. at N(K+2), for use in the next calculation but the counter 18' does not have its N value changed until a subsequent cycle when a decrement of N is detected in decision circuit 41. This is because of the averaging of values.

It will be seen that the selection of the constant predetermined value for $L_c$, which is set into preset block 24, is used in decision circuit 50 to determine when N(K) is decremented. The value for $L_c$ is conveniently selected by trial and error to give a desired accuracy without requiring too frequent determinations as the roll size increases. It has been found that a desirable selection of $L_c$ maintains very approximately, the same time interval between roll density determinations.

It is believed the previous description is sufficient for a complete understanding of the invention.

What we claim as new and desire to secure by Letters Patent of the United States of America is:

1. Apparatus for determining the density of a paper roll on a paper winding means comprising
   a paper receiving roll on said paper winding means for receiving a web of paper,
   means for feeding said web of paper onto said paper receiving roll,
   means for rotating said paper receiving roll to wind said web of paper onto said roll,
   means for providing a first signal representing the rotation of said paper receiving roll,
   counter means connected to said means for providing a first signal to receive said first signal and count the number of rotations of said paper receiving roll as represented by said first signal until a variable, preset count number N is reached for providing a second signal representing each count of N,
   memory means connected to said counter means to store the number of counts of N, the number of counts being represented by K,
   means to provide a third signal representing the length L of said web of paper wound on said paper receiving roll,
   comparison means for comparing said third signal with a preselected value representing length and for providing a fourth signal when said third signal exceeds said preselected value,
   means responsive to said fourth signal for decrementing N, and
   means for determining paper roll density at intervals represented by K or a multiple thereof.

2. Apparatus for determining the density of a paper roll on a paper winding means comprising
   a paper receiving roll on said paper winding means for receiving a web of paper,
   means for feeding said web of paper onto said paper receiving roll,
   means for rotating said paper receiving roll to wind said web of paper onto said roll,
   means to provide a first signal V respresenting the rotation of said paper receiving roll,
   counter means connected to said means to provide a first signal for counting rotations of said paper receiving roll represented by said first signal to a variable count number N and for providing a second signal representing each count of N,
   memory means connected to said counter means to store the number of counts of N represented as K,
   means to provide a third signal representing the the length L of said web of paper wound on said paper receiving roll at successive counts represented by K,
   comparison means for receiving said third signal, obtaining a difference value between two current successive lengths, comparing the difference value with a preselected value $L_c$ representing a length, and for providing a fourth signal when the difference is equal to or greater than said preselected value $L_c$,
   means responsive to said fourth signal for decrementing N,
   means responsive to said third signal and said value for N for deriving a value for roll diameter D for successive readings of L and N according to
   D = C L/N where C is a constant and for providing a fifth signal representing successive values of D for each successive K,
   means for receiving said fifth signal and providing a first average values $D(K-\frac{1}{2})$ for the diameter of two successive value of D and a second average value $D(K=\frac{1}{2})$ for the diameter of the next two successive readings and providing a sixth signal representing successive average values,
   means for receiving said sixth signal and determining a thickness t(K) according to $$t(K) = \frac{D(K + \frac{3}{2}) - D(K + \frac{1}{2})}{2} \cdot \frac{2 \cdot V}{[N(K) + N(K + 1)]}$$

and for providing a seventh signal representing successive values for thickness, and
   means for receiving said seventh signal and determining roll density d(K) for each thickness t(K) according to $$d(K) = \frac{m}{t(K)}$$

where m is the paper basis weight.

3. Apparatus as defined in claim 2 in which said means for rotating said paper receiving roll comprises a pair of horizontally spaced parallel first and second drums, said paper receiving roll being aligned with and supported by said first and second drums, and means for driving said first drum to cause rotation of said paper receiving roll.

4. Apparatus as defined in claim 3 in which said means to provide a third signal comprises a pulse generator connected with said first drum for providing pulses representing rotation of said first drum, said web of paper engaging a portion of said first drum as it moves onto said paper receiving roll, the pulses being counted at successive counts as represented by K giving lengths represented by L(K), L(K+1), L(K+2) and so on.

5. Apparatus for determining the density d of a paper roll on a paper winding means at substantially regular intervals of time, comprising
   first and second, parallel, horizontally spaced drums,
   a paper receiving roll supported by and aligned with said first and second drums,
   means for rotating said first drum at a substantially constant rate,
   means for feeding a web of a paper onto said first drum for engaging at least a portion of said first drum and extending onto said paper receiving roll to be wound onto said paper receiving roll as said first drum causes rotation of said paper receiving roll,
   first measuring means for measuring the rotation of said paper receiving roll and providing a signal V representing the rotation, second measuring means for measuring the rotation of said first drum and providing a signal Z representing the rotation, first counter means connected to said first measuring means for receiving said signal V representing rotations of said paper receiving roll, counting rotations to a variable count number N, and providing a count signal K representing the number of counts, memory means connected to said first counter means for storing the value for K, and the values V, Z and N for each K, second counter means connected to said second measuring means and to said first counter means for receiving said signal Z and said signal K and providing a count signal L for each K, the count signal L representing length at the time of each successive signal K, and count signal L being stored in said memory means, comparison means connected to said second counter means for determining a difference value L(K)−L(K−1) and for providing a change N signal when the difference value is greater than or equal to $L_c$ where $L_c$ is a preselected length value, means connected to the comparison means for receiving the change N signal and decrementing the value N for the next calculation of density according to the equation N(K+2)=N(K+1)−1, decision means initiated by the completion of each density calculation for determining if N has been decremented for the density calculation and in response to positive determination decrementing the count number N in the first counter means, and density calculation means connected to said memory means for receiving said signals Z, V, N and L for each K and determining density d according to the equation:

$$d(K-1) = \frac{Z \cdot m \cdot [N(K) + N(K-1)] \cdot N(K) \cdot N(K-1)}{D_D \cdot V^2 \cdot \{N(K-1) \cdot L(K) - [N(K) + N(K-1)] \cdot L(K-1) + N(K) \cdot L(K-2)\}},$$

where $D_D$ is the diameter of said first drum m is the paper basis weight.

* * * * *